United States Patent [19]

Bohning

[11] Patent Number: 4,855,910
[45] Date of Patent: Aug. 8, 1989

[54] TIME-CLUSTERED CARDIO-RESPIRATORY ENCODER AND METHOD FOR CLUSTERING CARDIO-RESPIRATORY SIGNALS

[75] Inventor: Daryl E. Bohning, Birmingham, Ala.

[73] Assignee: North American Philips Corporation, New York, N.Y.

[21] Appl. No.: 921,980

[22] Filed: Oct. 22, 1986

[51] Int. Cl.$^4$ ............................................. G01R 33/20
[52] U.S. Cl. .............................. 364/413.13; 324/309
[58] Field of Search .................. 364/413, 414, 413.13; 324/300, 309, 312; 128/653, 709, 711

[56] References Cited

U.S. PATENT DOCUMENTS

| | | | |
|---|---|---|---|
| 4,564,017 | 1/1986 | Glover | 128/653 |
| 4,614,195 | 9/1986 | Bottomley et al. | 324/309 |
| 4,663,591 | 5/1987 | Pelc et al. | 324/309 |
| 4,682,109 | 7/1987 | Cuppen | 128/653 |

OTHER PUBLICATIONS

Val M. Runge et al., "Respiratory Grating in Magnetic Resonance Imaging at 0.5 Tesla", 1984, pp. 521–523.
Wood and Henkelman Medical Physics, vol. 13, No. 6, Nov./Dec. 1986 "Suppression of Respiratory Motion Artifacts in Magnetic Resonance Imaging".

*Primary Examiner*—Jerry Smith
*Assistant Examiner*—Kimthanh T. Bui
*Attorney, Agent, or Firm*—Thomas A. Briody; Jack E. Haken; Jack D. Slobod

[57] ABSTRACT

A method and encoding system for retrospectively clustering NMR cardiac measurement profiles in cardio-respiratory phase planes, which method and system reduce cardio-vascular and respiratory flow motion image artifacts and provide quantitative characterizations of cardiac structure/function both with and without imaging. Profiles are clustered which are in the same relative positions in the cardiac cycles during which they were acquired, rather than in accordance with their positions relative to trigger pulses defining initiation of each cardiac cycle. This avoids artifacts due to irregular variations in the period of successive cardiac cycles.

4 Claims, 2 Drawing Sheets

TIME-CLUSTERED CARDIO-RESPIRATORY ENCODER AND METHOD FOR CLUSTERING CARDIO-RESPIRATORY SIGNALS

BACKGROUND OF THE INVENTION

1. Field of the Invention

This invention pertains generally to the field of nuclear magnetic resonance (NMR) tomography and in particular to retrospective clustering and analysis of NMR k-space measurements in the cardiac phase-respiratory phase plane. The processing system and method effect the reduction of cardio-vascular and respiratory flow motion artifacts in images and the quantitative characterization of cardiac structure and function both with and without imaging.

2. Description of the Prior Art

NMR spectroscopy, the process of analyzing a small sample in a uniform magnetic field and obtaining radio frequency data resulting from precisely pulsed radio frequency excitation, were invented by Block and Purcell. In the past 16 years, NMR analysis by spectroscopy has shifted from physical chemistry to biological chemistry and biological medical applications; i.e., biopsy samples of normal and diseased tissues. Lauterbur and Damadian and others separately invented the utilization of NMR principles to produce an image. (R. Damadian, Science 171,1151, 1971; P. C. Lauterbur, Nature 242, 190, 1973 and P. C. Lauterbur, Pure and Applied Chemistry, 40, 149, 1974). The resulting devices, NMR imaging systems, produced two dimensional and three dimensional data in which the gray scale represented is a function of a number of parameters, including for example the three parameters nuclide density, $T_1$ (longitudinal relaxation time) and $T_2$ (transverse relaxation time) especially in an anatomical image.

NMR imaging techniques are disclosed, for example, in "Proton NMR Tomography" P. R. Locher, Philips Technical Review, Vol. 41, 1983/84, No. 3, pages 73-88, the contents of which are incorporated herein by reference as a background of NMR imaging technology.

In vivo NMR imaging of biological tissue is rendered more difficult by movement of the biological tissue. This is especially true for example, in cardiac NMR imaging, as a result of the heartbeat. In order to prevent blurring and movement artifacts in cardiac NMR imaging, it is known to synchronize the measurements to the patients E.C.G., for example, as disclosed in U.S. Pat. No. 4,409,550, Fossel et al and U.S. Pat. No. 4,413,233, Fossel et al.

The noninvasive character of nuclear magnetic resonance (NMR) imaging and the absence of obscuration by bone structures make it a desirable technique for heart imaging. The relatively long scan times needed, however, give rise to motion artifacts. Synchronization of the imaging sequences to the heart cycle can greatly reduce these artifacts.

The capability of imaging in any phase of the cardiac cycle makes it possible to use NMR for volumetric measurements from end-systole and end-diastole images. Also, the evaluation of motion is possible by displaying images from consecutive phases in a movie loop. The use and benefits of NMR imaging for displaying the anatomy of the heart and great vessels, both untriggered and electrocardiogram (ECG) triggered, is well known. Apart from showing fine anatomical details in the heart, NMR heart imaging holds promise for tissue characterization as well, important for the detection and sizing of infarcts. Using velocity images, heart wall motion and blood flow speeds can also be quantitated with NMR imaging.

In the two-dimensional Fourier transform (2DFT) imaging method used, the NMR image is reconstructed from time signals by a complex 2DFT. For a 128×128 pixel image matrix, the signals are obtained in 128 consecutive imaging sequences or phases. For heart imaging, each imaging phase is triggered by a pulse derived from the R-wave of the patient's ECG. The delay of the pulse determines the imaging phase in the cardiac cycle. Each imaging phase consists of a series of radiofrequency (RF) and magnetic field gradient pulses, respectively, for evoking a signal and providing spatial information in the signal. A gradient magnetic field applied after an RF excitation pulse (90° pulse) makes the proton spins at different locations in the excited slice precess at different frequencies. The spins then start to dephase with respect to the resonant frequency phase. For a given cardiac location the associated phase shift of the spins is proportional to the gradient amplitude of the magentic field and the time it is active. There is, in addition, a difference in phase shift for stationary spins and moving spins. For spins moving uniformly in the direction of the gradient, an extra phase shift occurs that is directly proportional to the velocity in the gradient direction.

The present invention pertains to an improved method and system for correlating NMR data with data from cardiac/respiratory monitors commonly used for conventional cardiac triggering and respiratory gating. Many approaches to this problem have been tried in the prior art. NMR data collection has been started at fixed delays after the ECG R-wave, with possible rejection of abnormal R—R intervals. Typically, in the known arrangements, each data collection is started at some fixed time delay after the R wave peak. In a multiple cardiac slice study, data collection from successive slices continues until close to the next R wave peak. If the heart beats regularly, each measurement will take place at the same phase in the cardiac cycle.

In the event of arrhythmia, however, deviations of the heart's position will occur for some of the data collection, thereby giving rise to blurring and movement artifacts. Such arrhythmia will further lead to a variation in the R wave repetition period TR, resulting in an increased noise level and degradation of the precision of the phase measurements, as well as degrading the general image quality of the primary images, as noted by C. Galonad, D. J. Drost, S. S. Prato and G. Wisenberg, SMRM, Vol. 2, 1985. It is well known in nuclear medicine that rejection of data collection taken during and immediately after an arrhythmia improves image quality and consistency. In the past, however, it has been difficult to effect such data rejection in a simple and efficacious manner.

Respiratory cycle timing of the NMR k-space sampling has also been utilized. However, discarding abnormal physiological cycles, or physiological cycle correlated sampling of k-space, may actually cause abnormalities to be missed, which would defeat the diagnostic purpose of an NMR scan. Because of R—R. variation, cardiac triggering is less effective at the end of a heart cycle when coronaries fill and the pre-R-wave shape of the heart may give clues to contraction abnormalities.

The prior art approaches tend to be complicated combinations of slices, phases, triggers, delays, windows and data rejection and reordering imposed on the NMR data collection, causing problems with uncertain heart phasing, limited time resolution, and nonuniform spin saturation. The present invention is designed to overcome these problems.

SUMMARY OF THE INVENTION

The time-clustered cardio-respiratory encoder of the present invention is a microcomputer based system in which a microcomputer collects cardiac (C) R-wave time, respiratory (R) diaphragm position, and NMR data acquisition (A) timing data in parallel with free running image data collection by a microcomputer from a standard NMR scanner. After the raw data corresponding to multiple images has been collected, the C-A-R phase timing data are uploaded from the microcomputer to the minicomputer of the scanner for use in clustering the raw data into a new set of equivalent to one image for each cario-respiratory (C-R) phase combination desired. The position of an NMR profile in the normalized C-R phase plane determines the clustered image in which it will fall, i.e. which cardiac phase-respiratory phase combination. The clustered raw data are then filled and filtered to compensate for the nonuniform k-space sampling of the image data, and, finally, reconstructed with ordinary 2D or 3D Fourier Transform Techniques.

To obtain two multiple profile images, intended to show the heart at two different phases in its cycle, using the present invention one can obtain a time clustered image showing, for example, the first fifth of the cardiac cycle from all the profiles taken during the first fifth of the respective R—R intervals and a time clustered image showing the fourth fifth of the cardiac cycle from all the profiles taken during the fourth fifth of the respective R—R intervals.

The system is easily implemented with any NMR system and can be used with any pulse sequence. It requires only the output signals available from standard cardiac/respiratory monitors commonly used for conventional cardiac triggering and respiratory gating, and software parameter modifications to accommodate different pulse sequences, along with a timing signal from the NMR scanner.

The invention is a simple, flexible system for retrospectively clustering and analyzing NMR k-space measurement profiles in the cardiac phase-respiratory phase plane to: (1) reduce cardio-vascular and respiratory flow/motion image artifacts, and (2) to quantitatively characterize cardiac structure/function both with and without imaging.

DESCRIPTION OF THE PREFERRED EMBODIMENT

The invention pertains to a method and its implementation in an encoder for retrospectively clustering NMR k-space measurement profiles in the cardio-respiratory phase plane, which method and encoder function to: (1) reduce cardio-vascular and respiratory flow motion image artifacts, and (2) to characterize quantitatively cardiac structure/function both with and without imaging.

Figure 1:
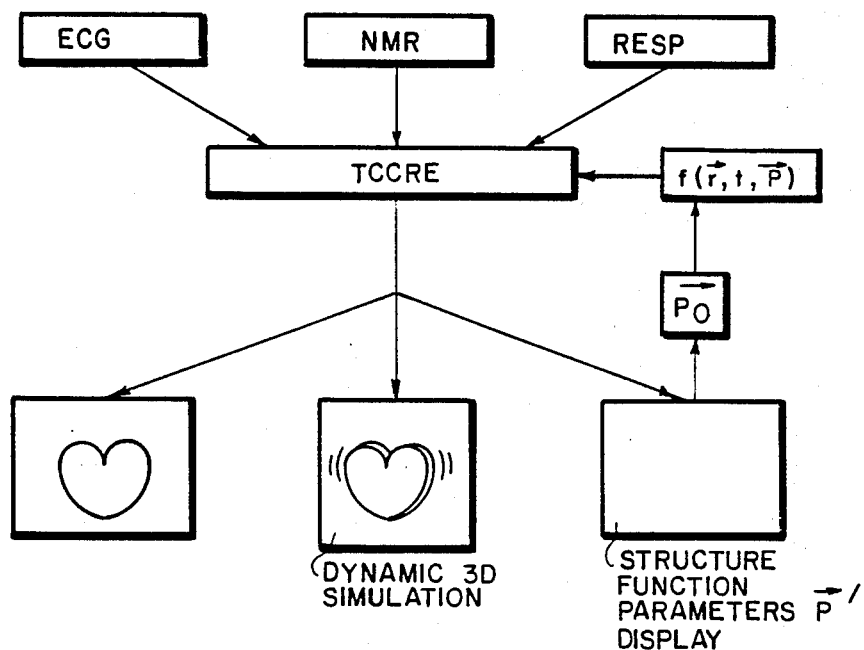
FIG. 1 is a functional block diagram showing the operation of time clustered cardio-respiratory encoder of the present invention within an NMR cardiac diagnostic system.

Referring to FIG. 1, phase marker data signifying, cardiac (C) time, respiratory (R) time corresponding to diaphragm position, and the NMR data acquisition cycle marker (A) are collected by a microcomputer in the TCCRE in parallel with free running, preferably steady state, image collection by the minicomputer of a standard NMR scanner. After collecting the raw data corresponding to multiple images, the C-A-R phase marker data are uploaded from the microcomputer to the minicomputer of the NMR scanner for use in cardio-respiratory plane clustering of the image data. The position of each NMR profile in the normalized C-R phase plane is determined and then clustered by the minicomputer into a new set of data, equivalent to one image for each desired C-R phase combination. The clustered data is then filled and filtered to compensate for the nonuniform k-space sampling, and finally reconstructed.

Figure 3:
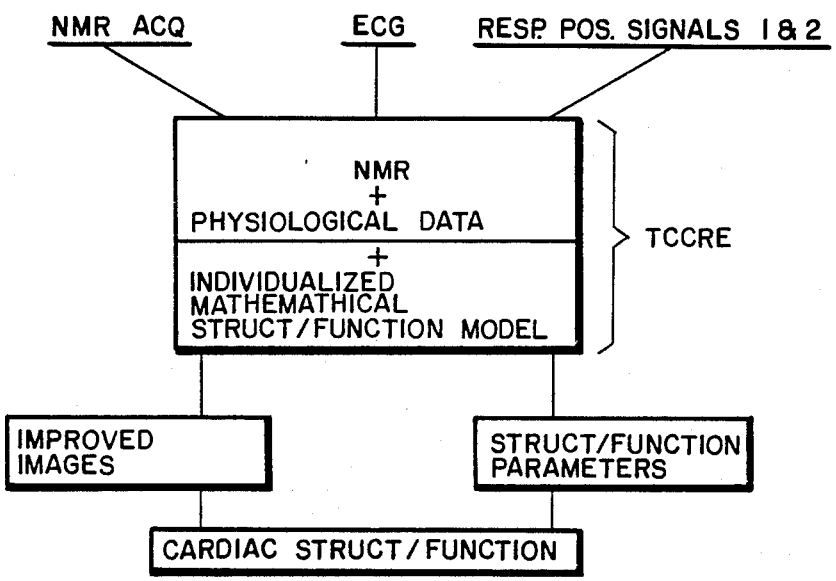
FIG. 3 is a functional block diagram of the method steps used in the time clustered cardio-respiratory encoder of the present invention.

The method of the present invention as illustrated in FIGS. 1 and 3 is as follows:

1. Collect NMR data profiles in the form of free running, possibly velocity encoded pulse sequence, while simultaneously collecting a digitized cardiac timing signal ECG:

$P(k\_x, k\_y, k\_z, t)$ and $EKG(t) \rightarrow EKG\_j(t); J\_th$ heart cycle.

2. Using a technique similar to that used for sorting serial nuclear medicine data, sort the NMR data profiles into normalized heart cycle time bins appropriate to the available signal to noise ratio, i.e. using time of the profile minus the time of the previous cardiac R-wave signal, all divided by the time of the following R-wave signal minus the time of the previous R-wave signal, to determine the time bin in which the NMR profile should be put. The NMR profile positions in the respiratory cycles are determined in the same way:

$P\_i(k\_x, k\_y, k\_z, t); i\_th$ phase of heart cycle
    $t\_i-1 < t < t\_i$.

These data form a set of (velocity) images, one for each heart cycle phase time bin, selected for moving heart tissue, but each image of the set possibly covering k-space incompletely, and a little differently.

3. Fit the data to a parameterized dynamic heart model, while still in frequency space.

4. Fill, filter and transform this data using a discrete, nonuniform, Fourier Transform to overcome the nonuniform k-space coverage.

5. Display if desired a dynamic simulation of the heart, along with its parameters, on an integrated graphics workstation.
6. Update, if desired, the dynamic heart model using the newly reconstructed data.

TCCRE images show less flow/motion artifacts and better heart visualization than comparably phased triggered images, especially towards the critical latter part of the cardiac cycle where coronary artery filling occurs.

As shown in FIGS. 1 and 3, the TCCRE receives digital cardiac R-wave signals C, analog or digital respiratory signals R and NMR data A acquisition timing data in parallel.

As shown in FIG. 3, the TCCRE integrates all NMR and physiological data, (e.g. cardiac R-wave and respiratory signals) that can be collected during an NMR scan or observation period with mathematical cardiac structure/function models and any data from previous time clustered cardio-respiratory encoder "scans" of the patient's heart. The result is as complete a characterization of the heart as possible, both with and without imaging. All the data is collected as quickly and as uniformly as possible, setting up an equilibrium of spin saturation and eddy currents that would make corrections for them along with magnetic field inhomogeneity easier. The integrated data is available for improving image quality or computing desired structure/function parameters. The output of the system is a dynamic three dimensional simulation of the heart and/or maximum likelihood fitted cardiac structure-function characterization parameters or images improved by the reduction of flow/motion artifacts.

Referring to FIGS. 1 and 3, the NMR and physiological timing signals used are an NMR pulse timing signal A, the cardiac ECG R-wave signal C, and analog diaphragm position respiratory signal S. These signals are collected throughout the measurement by the microprocessor of the TCCRE and are passed to a minicomputer is programmed to cluster the NMR k-space profile data in the reference frame of the normalized cardiac and respiratory cycles; i.e., in the C-R plane. A mathematical model can be applied to the data before and during reconstruction, and if desired the model can be modified with preexisting data. The processed data can be reconstructed into images which may be displayed, and/or structure/function parameters can be computed. The structure/function parameters can be used to derive a simulation of the beating heart. This is schematically illustrated in FIGS. 1 and 3.

The system is used for retrospectively clustering continuously collected NMR data with the ECG R-wave signal and digitized respiratory signal in the normalized C-R plane for the purpose of improving image quality.

Figure 4A:
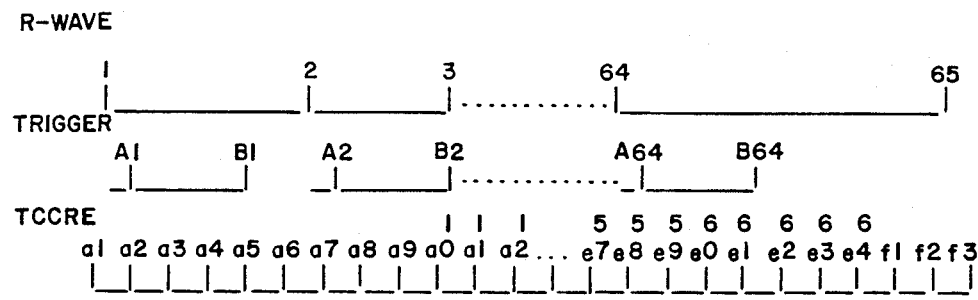
FIG. 4A is a plot showing the relationship of time clustered images to cardiac triggered images.

The diagram shown in FIG. 4A illustrates the collection of two different images, each having 64 clustered profiles, intended to show the heart at two different phases in each cardiac cycle, with no respiratory clustering. Referring to this diagram, TCCRE clustered image A, corresponding to the first 5th of the cycle, would then be formed from profiles: a2, a7, . . . , and e58. TCCRE clustered image B, corresponding to the fourth 5th of the cycle, would be formed from profiles a5, a9, e63, and e64. The short R2–R3 interval and long R64–R65 interval illustrate the problem with a fixed triggering delay in a variable heart cycle, profile B2 coming from the end of its R2 wave interval and profile B64 coming from the middle of its R64 wave interval.

Figure 4B:
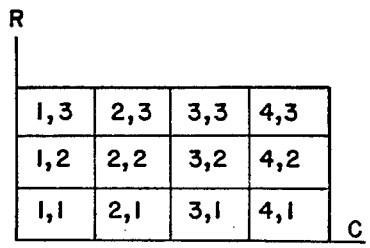
FIG. 4B shows a two dimensional clustering array of NMR image data such as may be provided by the encoder in the cardio-respiratory cycle plane.

If respiratory clustering is desired, each cardiac cluster would be smilarly broken down into clusters along the normalized respiratory cycle axis, say a 4×3 cardio-respiratory clustering, as shown in FIG. 4B.

Figure 2:
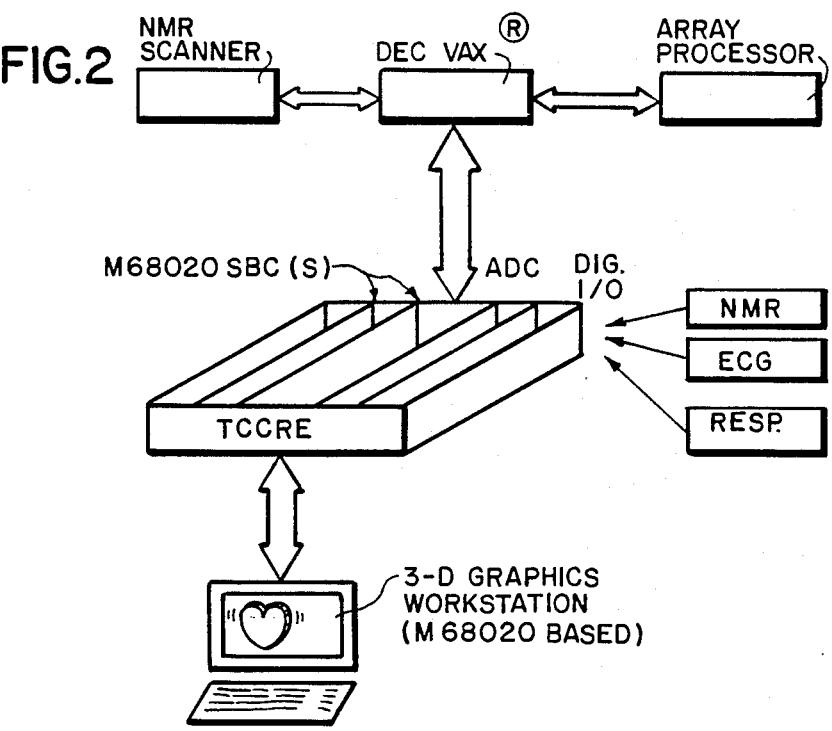
FIG. 2 is a hardware block diagram of the time clustered cardio-respiratory encoder of the invention within an NMR cardiac diagnostic system.

A system to implement the method of the invention is shown in FIG. 2. It includes microprocessor such as an M68020 in VME bus/power supply rack-mount chassis; a 4–8 channel ADC card; an 8 channel optically isolated digital I/O card; a digital input LATCH BOX with adjustable latching; a minicomputer such as a Digital Equipment Corporation: VAX/11/750 with array processor based software such as Philips' Flexible Reconstruction Package (FLEXIREC) for image reconstruction; and a graphics workstation with 3-D analysis and display software.

What is claimed is:
1. A system for obtaining imaging data of in vivo biological tissue subject to substantially periodic cardiac and respiratory cycles, which image data is sorted by phase intervals of the cycles comprising:
   a free-running NMR scanner means for collecting NMR data samples of said biological tissue without synchronization to the cycles, said NMR data samples requiring transformation of a plurality of said samples in order to produce image data therefrom;
   a transducer means for coupling to said biological tissue to detect cardiac and respiratory data simultaneously with the collection of NMR data samples by said NMR scanner; and
   data processing means receiving said NMR data samples and said cardiac and respiratory data, comprising:
   (a) means, utilizing said cardiac and respiratory data, for dividing each successive cycle into normalized time bins indicative of phase intervals of the cycle;
   (b) means for sorting the NMR data samples obtained during successive cycles into a two-dimensional array defined by the normalized time bins indicative of the phase intervals of the cycles during which said data samples were collected, and
   (c) means for transforming the sorted NMR data samples in the normalized time bins into image data corresponding to said time bins.

2. The system of claim 1, wherein said NMR scanner means collects data samples without synchronization to either of said cardiac and respiratory cycles.

3. A method for obtaining NMR image data of in vivo biological tissue subject to substantially periodic cardiac and respiratory cycles, which image data is sorted by phase intervals of the cycles comprising:
   (a) collecting NMR data samples of said biological tissue without synchronization to the cycles, said NMR data samples requiring transformation of a sequence of said samples in order to produce image data therefrom;
   (b) collecting cardiac and respiratory data indicative of the cycles simultaneously with the collection of NMR data samples;
   (c) dividing each successive cycle into normalized time bins indicative of phase intervals of the cycle, utilizing said cardiac and respiratory data;
   (d) sorting the NMR data samples obtained during successive cycles into a two dimensional array defined by the normalized time bins indicative of the phase intervals of the cycles during which said NMR data samples were collected; and after completion of said sorting;
   (e) transforming the sorted NMR data samples in the normalized time bins into image data corresponding to said bins.

4. The method of claim 3 wherein said collection of NMR data sample is without synchronization to either of said cardiac and respiratory cycles.

* * * * *